(12) United States Patent
Kieper et al.

(10) Patent No.: US 7,444,009 B1
(45) Date of Patent: Oct. 28, 2008

(54) METHOD TO IMPROVE CANCEROUS LESION DETECTION SENSITIVITY IN A DEDICATED DUAL-HEAD SCINTIMAMMOGRAPHY SYSTEM

(75) Inventors: Douglas Arthur Kieper, Newport News, VA (US); Stanislaw Majewski, Yorktown, VA (US); Benjamin L. Welch, Hampton, VA (US)

(73) Assignee: Jefferson Science Associates, Newport News, VA (US)

( * ) Notice: Subject to any disclaimer, the term of this patent is extended or adjusted under 35 U.S.C. 154(b) by 986 days.

(21) Appl. No.: 10/961,552

(22) Filed: Oct. 8, 2004

(51) Int. Cl.
*G06K 9/00* (2006.01)
*A61B 6/04* (2006.01)
(52) U.S. Cl. ........................ 382/128; 378/37
(58) Field of Classification Search ............... 382/128, 382/129, 130, 131, 132, 133, 134; 378/37; 600/407; 607/901; 128/915; 435/330; 436/64, 436/813
See application file for complete search history.

(56) References Cited

U.S. PATENT DOCUMENTS 5,519,221 A * 5/1996 Weinberg ............... 250/363.02

6,475,150 B2 * 11/2002 Haddad ....................... 600/448

* cited by examiner

*Primary Examiner*—Abolfazl Tabatabai

(57) ABSTRACT

An improved method for enhancing the contrast between background and lesion areas of a breast undergoing dual-head scintimammographic examination comprising: 1) acquiring a pair of digital images from a pair of small FOV or mini gamma cameras compressing the breast under examination from opposing sides; 2) inverting one of the pair of images to align or co-register with the other of the images to obtain co-registered pixel values; 3) normalizing the pair of images pixel-by-pixel by dividing pixel values from each of the two acquired images and the co-registered image by the average count per pixel in the entire breast area of the corresponding detector; and 4) multiplying the number of counts in each pixel by the value obtained in step 3 to produce a normalization enhanced two dimensional contrast map. This enhanced (increased contrast) contrast map enhances the visibility of minor local increases (uptakes) of activity over the background and therefore improves lesion detection sensitivity, especially of small lesions.

2 Claims, 1 Drawing Sheet

METHOD TO IMPROVE CANCEROUS LESION DETECTION SENSITIVITY IN A DEDICATED DUAL-HEAD SCINTIMAMMOGRAPHY SYSTEM

The United States of America may have certain rights to this invention under Management and Operating Contract No. DE-AC05-84ER 40150 from the Department of Energy.

FIELD OF THE INVENTION

The present invention relates to dual-head scintimammography techniques for the detection and localization of cancerous lesions particularly in breast examinations and more particularly to a method for combining the information provided by the opposing heads in a dual head system to maximize system sensitivity for cancerous lesions.

BACKGROUND OF THE INVENTION

Currently scintimammography imaging to detect breast cancer is performed with standard nuclear medicine cameras and it suffers from poor sensitivity for lesions under about 1 cm in diameter and lesions located in the medial aspect of the breast, away from the large camera surface. The main contributing factor to this poor performance is the poor spatial resolution during imaging due to the relatively large distance between the lesion and the collimator of the detector head.

The development of compact small field of view (FOV) cameras/detectors, allowed for the placement of the camera directly against the breast thus significantly minimizing spatial resolution effects by minimizing the target to collimator distance. Testing and evaluation of these small FOV cameras in direct contact with the breast provided the expected increase in detection sensitivity for small lesions. However it was apparent that lesion-to-camera distance still had a strong impact upon lesion detection and even these dedicated instruments can show substantial sensitivity variation depending on lesion position within the breast. By incorporating a second camera/detector on the opposite side of the breast, total target-to-detector distance was further minimized.

In 2001, Majewski et al. (S. Majewski, E. Curran, C. Keppel, D. Keiper, B. Kross, A. Pulumbo, V. Popov, A. G. Weisenberger, B. Welch, R. Wokjcik, M. B. Willimas, A. R. Goods, M. Moore, and G. Zheng, Optimization of Dedicated Scintimammography Procedure Using Detector Prototypes and Compressible Phantoms, *IEEE Trans. Nucl. Sci*, vol 48, no. 3, pp 822-829, June 2001) proposed a system implementing two identical and opposed detector heads placed on either side of a breast under compression to provide an optimal imaging geometry. While this improved approach confirmed that the dual head system is especially useful in most clinical situations where lesion location is not known a priori, the remaining important issue was how to combine most efficiently the two images obtained from the double sided imaging.

In a paper published in 2002, Kieper et al. (D. Kieper, S. Majewski, V. Popov, M. F. Smith, A. G. Weisenberger, B. Welch, R. Wojcik, M. B. Williams, M. J. Moore, and D. Narayanan, "Improved Lesion Visibility in a Dedicated Dual-Head Scintimammography System—Phantom Results", submitted for publication at the 2002 IEEE Medical Imaging Conference, Norfolk, Va., Nov. 7-19, 2002) further proposed to enhance lesion detection and localization by enhancing the contrast value through the application of a geometric mean technique involving the use of the square root of two registered images, one from each of the two cameras used to compress the breast from opposing sides. This technique further enhanced lesion vs. background contrast, but still did not produced the degree of contrast desired.

Accordingly, there remains a need to further enhance lesion vs. background contrast to more accurately characterize and localize potentially cancerous lesions.

OBJECT OF THE INVENTION

It is therefore an object of the present invention to provide a methodology for the further enhancement of the contrast between background and lesion areas of a breast undergoing dual-head scintimammography examination.

SUMMARY OF THE INVENTION

According to the present invention, there is provided an improved method for enhancing the contrast between background and lesion areas of a breast undergoing dual-head scintimammographic examination comprising: 1) acquiring a pair of digital images from a pair of small FOV or mini gamma cameras compressing the breast under examination from opposing sides; 2) inverting one of the pair of images to align or co-register with the other of the images to obtain co-registered pixel values; 3) normalizing the pair of images pixel-by-pixel by dividing pixel values from each of the two acquired images and the co-registered image by the average count per pixel in the entire breast area of the corresponding detector; and 4) multiplying the number of counts in each pixel by the value obtained in step 3 to produce a normalization enhanced two dimensional contrast map. This enhanced (increased contrast) contrast map enhances the visibility of minor local increases (uptakes) of activity over the background and therefore improves lesion detection sensitivity, especially of small lesions. It also increases lesion sensitivity independently of lesion position within the breast volume.

DETAILED DESCRIPTION

Figure 1:
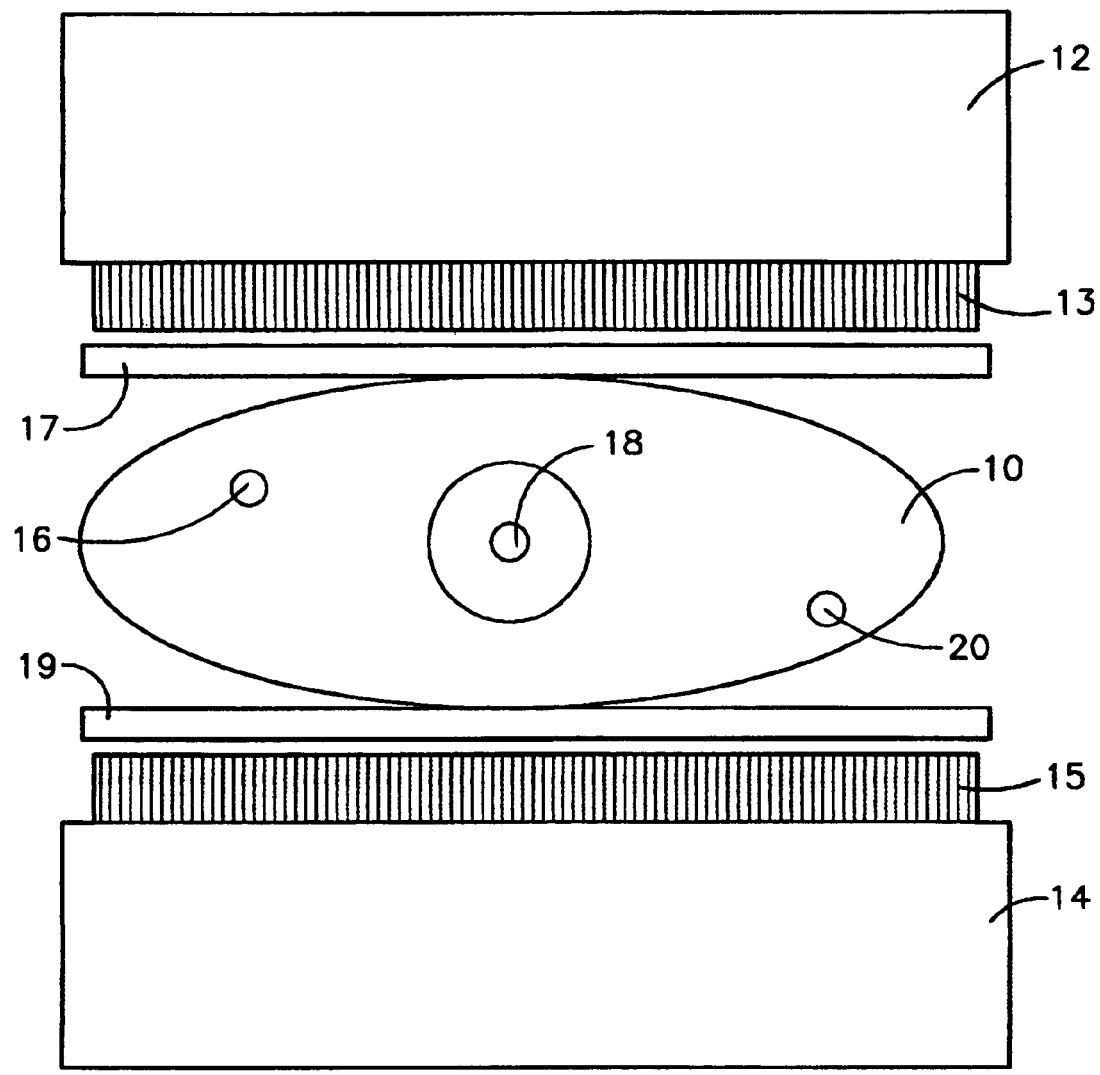
FIG. 1 is a schematic depiction of the same breast under compression between two compact gamma camera detector heads.

So called mini gamma or small field of view (FOV) cameras and their methods for use are well known in the art (see for example U.S. Pat. No. 6,271,525 to Majewski et al. whose description is incorporated herein by reference in its entirety) and commercially available from at least two sources: Dilon Technologies, 12050 Jefferson Ave., New Port News, Va. 23606; and Gamma Medica™, Inc., 19355 Business Center Drive, Suite 8, Northridge, Calif. 91324. Such cameras have been routinely applied to the examination of breasts for the presence of lesions by a process that involves injection of the patient with a radiopharmaceutical and examination of the breast with the mini gamma camera to detect differences in the uptake of the radiopharmaceutical between normal tissue and areas containing lesions.

In the 2002 paper by Kieper et al. described above, it was proposed to enhance lesion detection and localization through the use of a pair of opposed mini gamma cameras compressing the breast directly from opposite sides to obtain a pair of images, co-registering the images and enhancing the contrast value of the co-registered image through the application of a geometric mean technique involving taking the square root of two registered images, one from each of the two cameras used to compress the breast from opposing sides.

While, as stated above, this approached proved highly useful and did indeed result in enhancement of the images further increase in contrast between the normal background and lesion areas of the breast, particularly in the detection of small lesions, <about 1 cm, was desired.

We have now discovered a better method for combining the information provided by the opposing detector heads as proposed by Kieper et al. to maximize system sensitivity for cancerous lesions.

In accordance with the present invention, the breast tissue 10 is first compressed between two opposing, mini gamma camera detector heads 12 and 14 including collimators 13 and 15 and gamma transparent faces 17 and 19 as shown in FIG. 1, preferably in the absence of additional passive compression paddles. This compression geometry maximizes the spatial resolution by minimizing the average detector-to-lesion distance as discussed above, and minimizes the absorption and scatter effect of radiation emitted by the lesion by, on average, decreasing the amount of benign tissue between the lesion and the detector heads. Additionally, it minimizes the thickness of overlaying breast tissue to be imaged and therefore enhances lesion contrast by minimizing background emitted by that benign tissue. This technique is described in detail in the aforementioned Kieper et al. paper that is also incorporated herein by reference in its entirety.

The imaging process of the present invention differs from that of Kieper et al. in it use of a novel image normalization/fusion technique that provides a two dimensional contrast map of the breast that is the result of multiplying the normalized pixel values of each of the two images together. The advantages of the use of the method of the present invention will be clearly demonstrated by a direct comparison of the results of contrast maps obtained by the method of Kieper et al. and that of the instantly described method.

In order to demonstrate the enhanced results of the method of the present invention over those of Keiper et al., the methodology of Kieper et al. was replicated. A compressible breast phantom was constructed from gelatin filler mixed with Tc-99 sodium pertecnitate in solution encapsulated in a latex outer skin to simulate breast tissue. Three plastic lesion spheres were filled with a specific activity six times greater than that of the gelatin mix and then introduced into the breast phantom as shown at 16, 18 and 20 in FIG. 1. The left lesion (16 in FIG. 1) had a diameter of 0.6 cm the center lesion (18 in FIG. 1) a diameter of 0.8 cm and the left lesion (20 in FIG. 1) a diameter of 0.45 cm. The exact method of preparing flexible gelatin breast phantoms is well known in the art and is described in detail in the following paper, S. Majewski, E. Curran, C. Kepple, D. Keiper, B. Kross, A. Pulumbo, V. Popov, A. G. Weisenberger, B. Welch, Wojcik. M. B. Williams, A. R. Goode, G. Moore, and G. Zang, "Optimization of Dedicated Scintimamography Procedure Using Detector Prototypes and Compressible Phantoms", *IEEE Trans. Nucl. Sci.* 2001, 48(3): 822-829, which paper is incorporated herein in its entirety for its description of the method of preparing gelatin based breast phantoms. The breast phantom containing the inserted "lesions" was then compressed to 6 cm +/−1.5 cm between two opposing mini gamma cameras as shown in FIG. 1. This experimental set up is identical to that used by Keiper et al. As reported by Keiper et al., contrast results for each of the three lesions and the combined image results obtained using the geometric mean technique, square root (image 1* image 2) are as shown in Table 1 below.

TABLE 1

|  | Left lesion 0.6 cm dia. | Center Lesion 0.8 cm dia. | Right Lesion 0.45 cm dia. |
|---|---|---|---|
| Detector 1 | 1.25 | 1.28 | 1.07 |
| Detector 2 | 1.11 | 1.31 | 1.04 |
| Combined Image | 1.38 | 1.69 | 1.13 |

In contrast to the above results when the identical opposed, dual camera, compression experimental arrangement (as shown in Figure) was used but the contrast was enhanced using the image normalization/fusion technique of the present invention, the results were as shown in Table 2 below.

TABLE 2

|  | Left lesion 0.6 cm dia. | Center Lesion 0.8 cm dia. | Right Lesion 0.45 cm dia. |
|---|---|---|---|
| Detector 1 | 1.73 | 1.65 | 1.39 |
| Detector 2 | 1.95 | 1.61 | 1.16 |
| Combined Image | 3.38 | 2.68 | 1.61 |

In the tests performed in accordance with the present invention, the positions of cameras 12 and 14 were geometrically aligned to better than 1 mm so as to achieve a one-to-one pixel correspondence. In the first step, the image from second camera 14, initially vertically mirror-reflected relative to first camera position 12, was inverted to align (co-register) with the first image obtained from first camera 12. Using the average count per pixel in the entire breast area of the corresponding detector as a normalization value, the number of counts in each pixel was divided by that normalization value. Thus, pixel values at or near background level became equal to a value near one while any meaningful lesion signal produced normalized pixel values greater than one. The normalized images from each detector were then multiplied pixel-by-pixel to combine and "magnify" the presence of co-registered focal hot spots. As shown above, the use of this technique indeed enhanced the visibility of the small lesions.

There has thus been described a method for enhancing the sensitivity of scintimammographic images to the presence of especially small lesions in a dual-head/opposing view mini gamma camera system. The availability of such enhanced sensitivity will further increase the diagnostician's ability to identify and locate ever smaller potentially cancerous lesions at ever earlier time thereby advancing the start of remedial treatment.

As the invention has been described, it will be apparent to those skilled in the art that the same may be varied in many ways without departing from the intended spirit and scope of the invention, and any and all such modifications are intended to be included within the scope of the appended claims.

What is claimed is:

1. An improved method for enhancing the contrast between background and lesion areas of a breast undergoing dual-head scintimammographic examination comprising:
   1) acquiring a pair of digital images from a pair of small FOV or mini gamma cameras compressing the breast under examination from opposing sides;
   2) inverting one of the pair of images to align or co-register with the other of the pair of images to obtain a co-registered image and co-registered pixel values;
   3) normalizing the pair of images pixel-by-pixel by dividing the pixel values from each of the two acquired images and the co-registered image by the average count per pixel in the entire breast area of the corresponding detector; and 4) multiplying the number of counts in each pixel by the value obtained in step 3 to produce a normalization enhanced two dimensional contrast map of the breast.

2. The method of claim 1 wherein the breast is directly compressed by the opposing mini gamma cameras.

* * * * *